United States Patent [19]
Finley

[11] Patent Number: 5,709,470
[45] Date of Patent: Jan. 20, 1998

[54] METHOD AND APPARATUS FOR DETECTING ICE BUILDUP

[75] Inventor: Charles M. Finley, Arcadia, Calif.

[73] Assignee: CNC Development, Inc., Arcadia, Calif.

[21] Appl. No.: 499,863

[22] Filed: Jul. 10, 1995

[51] Int. Cl.⁶ .................................................. G01N 25/04
[52] U.S. Cl. ........................... 374/16; 374/164; 340/580
[58] Field of Search ............................. 374/16, 21, 25, 374/164, 173; 340/580, 581

[56] References Cited

U.S. PATENT DOCUMENTS

| | | | |
|---|---|---|---|
| 2,766,619 | 10/1956 | Tribus et al. | 73/170 |
| 3,000,213 | 9/1961 | Eves et al. | 73/149 |
| 3,594,775 | 7/1971 | Fox | 340/234 |
| 4,046,509 | 9/1977 | Bäckerud | 374/25 |
| 4,327,286 | 4/1982 | Thoma | 250/231 R |
| 4,329,682 | 5/1982 | Baker | 340/581 |
| 4,333,004 | 6/1982 | Forgue et al. | 219/497 |
| 4,383,770 | 5/1983 | Boschung et al. | 374/25 |
| 4,808,009 | 2/1989 | Sittler et al. | 374/25 |
| 4,819,480 | 4/1989 | Sabin | 340/581 |
| 4,980,673 | 12/1990 | Kleven | 340/581 |
| 5,000,579 | 3/1991 | Kumada et al. | 374/16 |
| 5,003,295 | 3/1991 | Kleven | 340/581 |
| 5,108,193 | 4/1992 | Furubayashi | 374/164 |

*Primary Examiner*—G. Bradley Bennett

[57] ABSTRACT

A measuring system for the detection of ice buildup on aircraft in flight is described. It depends for its action on a well-known physical phenomenon called "heat of fusion" and senses the heat required to melt ice back to liquid water. The energy signal that is measured can only be produced by an ice-to-water transition, hence this system uniquely identifies the presence or absence of ice without regard to time, temperature, altitude, pressure or other factors. The system is capable of generating a rapid, real-time electrical signal that can be displayed to and readily understood by crew members, so that corrective action may be taken to safeguard the operation of the craft.

12 Claims, 6 Drawing Sheets

METHOD AND APPARATUS FOR DETECTING ICE BUILDUP

FIELD OF THE INVENTION

The invention relates to detecting the presence of ice in a fluid sample, and particularly, to detecting in a timely manner the in-flight buildup of ice on aircraft surfaces, particularly control and lift providing surfaces, so that corrective measures can be taken if needed for the aircraft's safety.

BACKGROUND OF THE INVENTION

Airplanes depend upon a number of specialized surfaces to provide lift and control during flight. It is frequently observed, during certain weather conditions, that ice can form on these surfaces while the airplane is in flight and consequently can create a hazard to safe operation. Such occurrences are particularly serious if the plane is at a relatively low altitude or at a low speed. Both of these conditions (low altitude, low speed) occur when an airplane is coming in for a landing, and a number of aircraft disasters have been traced to ice forming on lift and control surfaces during this critical maneuver.

To avoid the possibility of unsuspected or very rapid ice formation, a reliable detection system is needed that can communicate the onset and buildup of icing to the crew well in advance of the point where the amount of ice that has formed represents a danger to the safe operation of the aircraft. It must not signal the presence of ice when there is none and, most importantly, must not signal "no ice" when ice is present.

This invention addresses itself to that need and has the ability to provide a sensitive, error-free, automatic indication of ice formation through sensors located at strategic places on the aircraft. The sensors will continue to show the presence of ice so long as it is there, and further, the nature of the sensors permits the rough estimation of the thickness of the ice on a given sensor. The sensors can be made both small and rugged, and through relatively simple electronic circuitry can be read out into a display easily interpreted by the pilot or other crew members. The detection principle prevents the reporting of ice when there is none, and vice versa.

Many different types of systems for detecting ice and icing conditions have been proposed. They have been based on a variety of approaches: optical, electrical, thermal and even nuclear. None have demonstrated sufficient reliability to the aircraft industry to be adopted as a standard part of an aircraft's instrument package. However, those based on an electrical approach have come closest to providing a practical answer to the problem.

Most prior art approaches that produce useful results, at least some part of the time, depend primarily upon certain temperatures being achieved by a sensor or sensors, or certain temperature differences occurring between two or more sensors, etc. All of these are bound to fail unpredictably because no particular temperature or temperature difference can always be counted on to show the presence or absence of ice, as there is nothing truly unique about the presence or absence of ice to cause either a particular temperature or temperature difference to come about.

Other prior art devices have attempted to utilize the heat of fusion (or melting) which is required to change the state between solid ice and liquid water. In such known systems, the length of time a temperature sensor that is being heated may require to go from a temperature below the freezing point of water to one above the freezing point of water can be markedly different if ice is initially present on the sensor than if it is absent. By detecting this variation in time, which is obviously related to the melting phenomenon, one can determine if ice is initially present, since the time is longer than if ice is not present. But these methods still depend upon the melting temperature of water being known during the measuring period in order to bracket it and produce reliable results. More importantly, they also lack any truly unique way to signal that ice does or does not exist, since under very warm or cold conditions, at high or low air flow velocities, when the air pressure is very high or low, etc., the time for a sensor to warm across the chosen range of temperatures might be either long or short, whether ice is present or not, and no particular amount of time can be said to unequivocally represent the presence or absence of ice or of any given quantity of ice. Thus methods based on some particular temperature change and/or on the time of some particular change also are bound to prove insufficiently reliable, and so have not been adopted for regular use by the aircraft industry.

SUMMARY OF THE INVENTION

The present invention depends upon the well-known physical phenomenon, the heat of melting of ice that accompanies this change of state, for the creation of the signal that indicates that ice is or is not present. It is not dependent in any way upon the measurement of time, nor upon the measurement of the absolute temperature, as factors in determining an answer. A benefit conferred by this approach is that the time required to make a measurement can be preset and relatively invariant, and usually will be much shorter than the time required by methods utilizing time as the measured variable.

The melting point of water is well known and is at or about zero degrees Centigrade, depending upon the water's purity and the atmospheric pressure. It is generally very sharp; that is, the change of state from solid to liquid or vice versa occurs with a barely discernible change in temperature, even for impure water. Per gram, the amount of heat energy needed for this change of state is much larger than the heat capacity of either ice or liquid water, allowing simple, rugged electrical components and circuitry to be used for detection purposes.

If a thermometer or other temperature sensing device is immersed in water that is brought to the freezing point by the slow removal of heat, it will be seen that the temperature declines steadily until the freezing point is reached and then stops falling until all of the water has turned to ice. Then the temperature will resume its decline. A similar but reversed observation will be made if ice is caused to warm at some steady rate: the temperature will cease rising when the melting point is reached until all of the ice has melted, and will then resume its climb. These "halts" in the temperature-versus-time curves are the direct result of the extra energy absorbed or given up at the point where this change of state occurs.

The present invention does not depend upon measuring the length of time of such halts or the temperature at which they occur. Instead, a constant rate of temperature increase is demanded by the electronic circuitry (e.g., one degree per second) and accomplished by applying sufficient power to a heater to cause that result, over a range of temperature that extends beyond the expected melting point of water ice. The amount of power needed by the heater is monitored by a small computer to see if it stays relatively constant (which would indicate that no melting phenomenon had occurred within the range of temperature scanned), or if at some point, the exact temperature being unimportant, a large upsurge in power is required (indicating that energy for melting of ice had been needed, and delivered, over a very short period of time). Once that energy surge subsides and has been measured, the electronic circuitry can remove power from the heater and allow the entire system to reset for the next measuring cycle. This permits the cycle time to be shorter, since no scan to a higher temperature is needed.

The invention utilizes a small temperature sensor such as (but not limited to) a thermocouple, closely connected (thermally but not necessarily electrically) to a small heater. This assembly is positioned in a way that exposes it continuously to the potentially ice-forming environment and is connected to electronic circuitry that powers the heater, senses that ice is or is not present by looking for a power surge, and delivers a signal via a small, dedicated computer resulting in an alarm message to the aircraft's crew if ice has begun forming.

Such an energy surge can only occur if ice was initially present. If it was not present, and perhaps only air or water were in contact with the sensor initially, the steady energy input needed to cause a steady rise in temperature may be different from situation to situation, but no violent upsurge in energy input will occur as the sensor temperature crosses the melting point of ice, because there is no ice to melt. Furthermore, the exact melting point of ice under whatever conditions of air temperature or flow or pressure, etc., need not be known in advance. If the temperature is forced to rise to several degrees above zero degrees Centigrade, the melting point (at whatever temperature it is) certainly will be crossed and an upsurge in driving energy to the sensing device either will or will not occur. If ice is initially present, it will clearly signal that fact when it melts by requiring a sudden, large upsurge in energy; if no ice is present initially, then no upsurge will occur and no signal suggesting that it was will be generated. The energy requirement for ice present as compared to ice absent will be very large at the melting point, wherever it is, and no uncertainty about the meaning of this unique upsurge is possible, as there are no other substances (air, liquid water, oil, fuel, the materials of construction of the aircraft, etc.) present that can undergo a change of state at or near zero degrees Centigrade.

BRIEF DESCRIPTION OF THE DRAWINGS

Various aspects of the invention will be better understood by examining the accompanying drawings, wherein.

DETAILED DESCRIPTION

The truly unique thing about the melting (or freezing) phenomenon for any material is the large amount of heat related to such a change of state compared to the heat capacity of the material at temperatures away from the melting point. Water ice, for example, has a heat capacity of about 0.5 calories per gram per degree Centigrade, liquid water has a heat capacity of about 1.0 calories per gram per degree Centigrade, and the heat required to melt ice into water is about 80 calories per gram. This large amount of heat energy associated with melting can easily be observed by forcing the temperature of ice to increase at some constant rate until the melting point is reached, while monitoring the amount of energy that must be put in to cause the steady rise in temperature, and then continuing to force the temperature to rise at the same steady pace on through the melting point. Under this condition the ice must turn to liquid water almost instantly, necessitating a very large upsurge in the power requirement of the heating element used to drive the temperature upwards. Depending upon the degree to which all of the ice can be induced to melt at the same time, the energy surge can certainly be tens, and perhaps hundreds, of times greater for a very brief period than the average energy level required by the ice prior to melting, or by the resultant water after melting.

Figure 3:
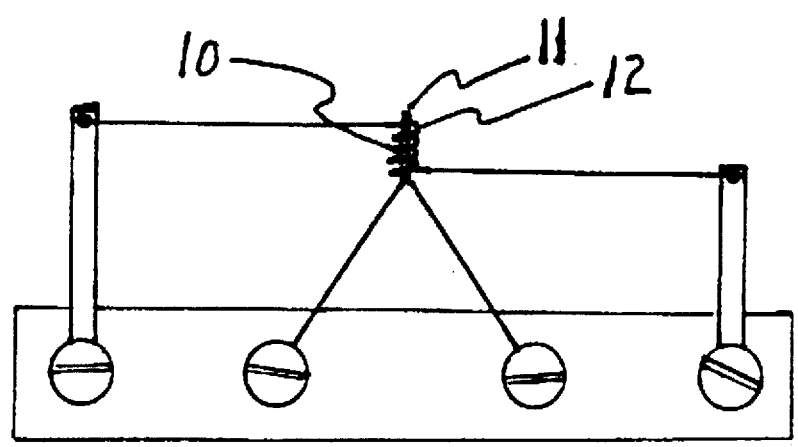
FIG. 3 shows one example of a heater-sensor embodiment with a small resistance heater wound over a small thermocouple junction.

The present invention is based on this unique characteristic known as the heat of fusion. In its simplest form, the invention utilizes a heater/sensor assembly 10 (see FIG. 3) which includes a temperature sensor 11. The sensor 11 consists of a thermocouple, thermistor, temperature-sensitive resistor or any other temperature sensitive device that can conveniently provide a temperature indicating signal to the controlling electronic circuitry. The temperature sensor 11 is tightly coupled thermally to a heater 12 of appropriate size. This heater may be in the form of a winding, a ribbon, a bead or any other shape or size that permits effective and rapid heating of the sensor, and which is easily controlled by the electronics. The heating element could also be a Peltier device. These semiconductor devices will generate heat if direct current is passed through them in one direction, and will absorb heat (i.e., cool) if heat is passed through them in the opposite direction. This cooling capability might be useful in enabling the sensor to reach equilibrium with the environment and thus reduce the time needed for the measurement cycle.

The heater and temperature sensor may be connected to one another electrically as well as mechanically and thermally, but in the preferred embodiment they are electrically isolated. This eliminates the possibility of electrical cross-talk between the heater and the sensor, and allows for the use of AC in one part of the circuit, if desired (in the heater, for example), while DC is used in another.

Figure 4:
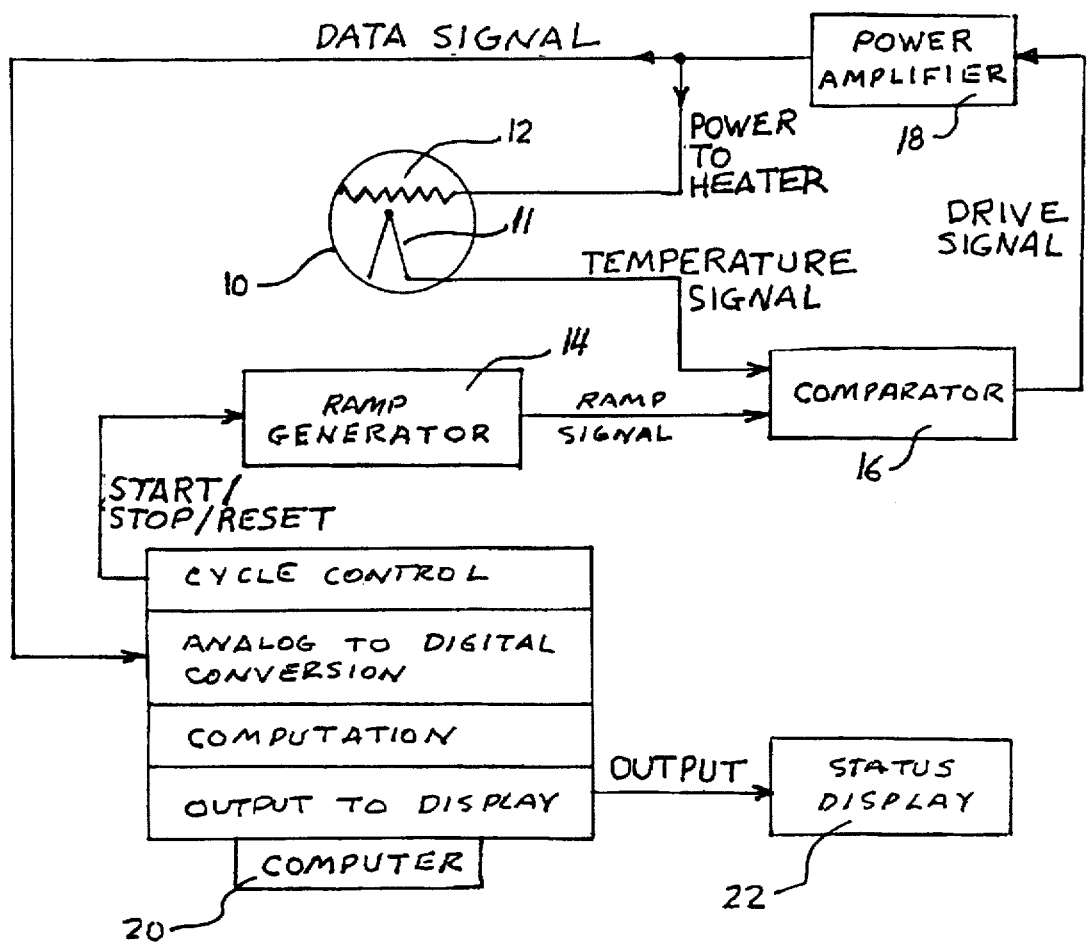
FIG. 4 illustrates electronic circuitry capable of producing a constant rate of temperature increase of a fluid sample and measuring any surge in energy if ice is present in the sample.

The preferred electronic circuitry (FIG. 4) consists of a ramp generator 14 feeding a comparator 16 that is also fed from circuitry connected to the output of the temperature sensor 11. The comparator output drives the amplifier 18 that delivers power to the heater 12. In this arrangement, a difference between the ramp value and the value fed back from the sensor is amplified and applied to the heater so as to minimize that difference; thus power delivered to the heater varies as required to cause the temperature of the sensor to move up steadily at the rate determined by the ramp generator.

Figure 1:
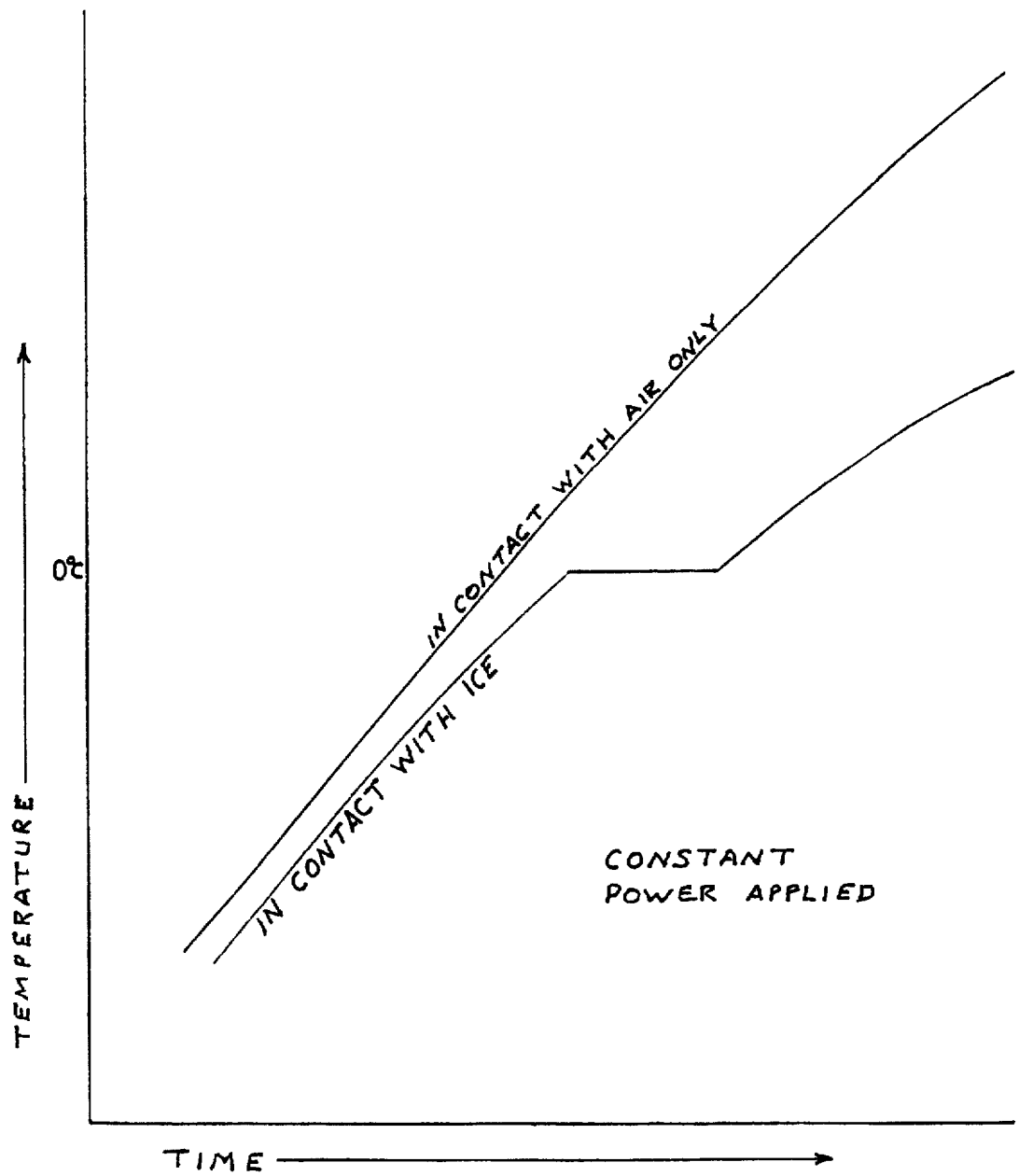
FIG. 1 illustrates the temperature-versus-time characteristics for a heater-sensor assembly 1) in contact only with air and 2) in contact with ice, when constant power is applied to the heater.
Figure 2A:
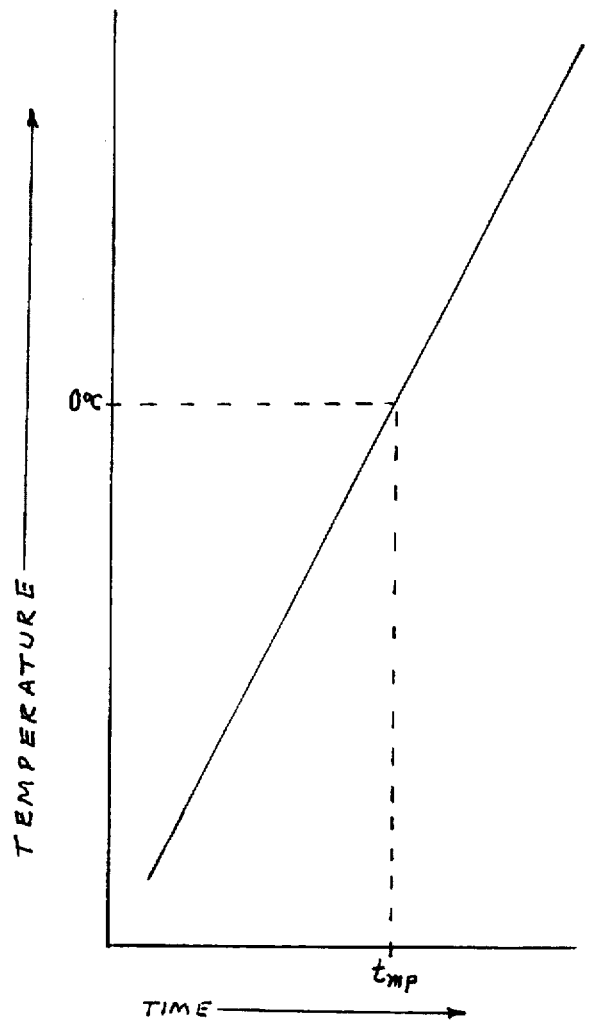
FIG. 2a illustrates the temperature-versus-time curve for a heater sensor assembly in contact with air or in contact with ice, when the temperature is driven upwards at a constant rate by varying the power applied to the heater as needed.
Figure 2B:
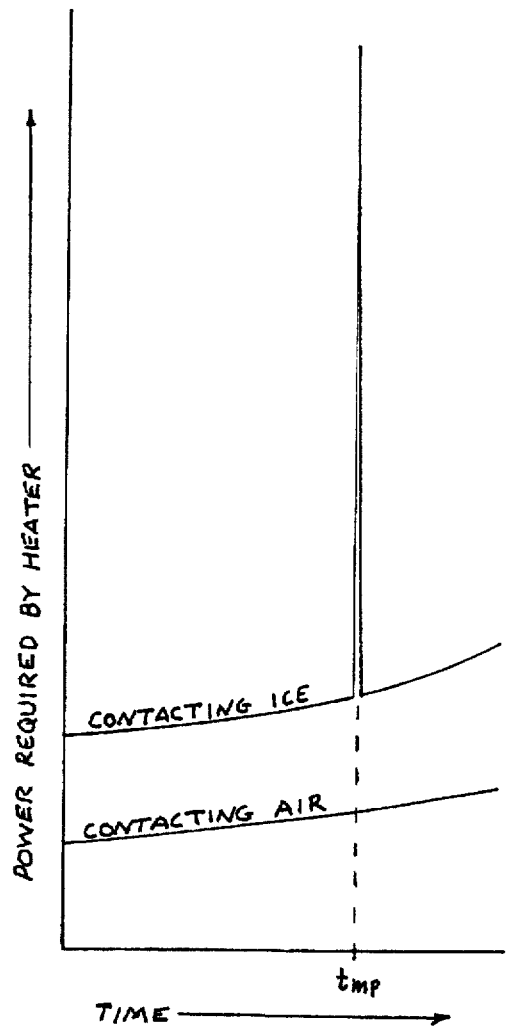
FIG. 2b illustrates the power delivered to the heater under these same conditions: 1) when ice is absent (i.e., air only) and 2) when it is present.

The level of power driving the heater at any time is monitored by a computer 20 and, from the presence or absence of a "spike" in power demand, as shown in FIG. 2b, and the magnitude of such a spike if present, the computer decides if ice has formed and makes an estimate of its thickness and rate of formation. The result is then applied to a suitable display device 22 to alert the operator of the condition. Heater power is removed when an appropriate temperature has been reached (1 or 2 degrees Centigrade might be selected), or immediately after ice has been detected, and the heater-sensor assembly 10 is then allowed to cool down and ice up again before power is once more applied.

In operation, no power is initially applied to the heater, so the sensing assembly would be at the temperature of its surroundings. It is immersed in a fluid sample of either dry air, water (if a non-freezing rain was falling) or ice (if a freezing rain was falling). Once the measuring cycle is begun, power is applied to the heater to whatever extent is needed to accomplish a preset rate of temperature rise with time. In either of the two cases where ice is not present (sensor in contact with air only, or sensor in contact with air and/or liquid water only), the power applied to the heater remains constant or slowly rises in a smooth way as the temperature increases at its preset rate to whatever preset end-of-measurement temperature in excess of the melting point of ice has been selected (perhaps 1 or 2 degrees Centigrade). At that time heater power is removed and the heater-sensor assembly allowed to cool back to whatever the ambient or start-of-measurement temperature might be. In particular, no sudden upsurge to a very high power level for a brief period would be observed. Thus no "ice present" signal is generated.

If ice is present, however, the power to the heater remains constant or rises slowly and smoothly only until the melting point of the ice is reached. Then, because the electronic circuitry tries to maintain a steady increase of temperature with time, a large amount of heat energy is required in a very short time to melt the ice. As a result, the power level at the heater is increased very dramatically. This lasts for a brief period of time required to melt the sample ice and then the power being applied to the heater falls back to some steady value at or near the original level. The amount of extra energy that has to be delivered to accomplish this melting of the ice clearly is related to the quantity of ice that has to be melted. The power to the heater is then removed at once after the power input of the heater falls back from the surge level and the assembly is allowed to re-equilibrate with its environment, including the reformation of ice on the assembly, for whatever time is appropriate, typically a few seconds.

This entire cycle is repeated, on as rapid a basis as possible, to give information to the electronic circuits providing a readout to the crew of the aircraft. Heater-sensor assemblies located at a number of points can provide data for all critical areas. The heater-sensor assemblies can be made as small as the head of a pin or as large as desired, and the cycle time can be as short as a few tens of seconds or a few minutes.

Figure 5:
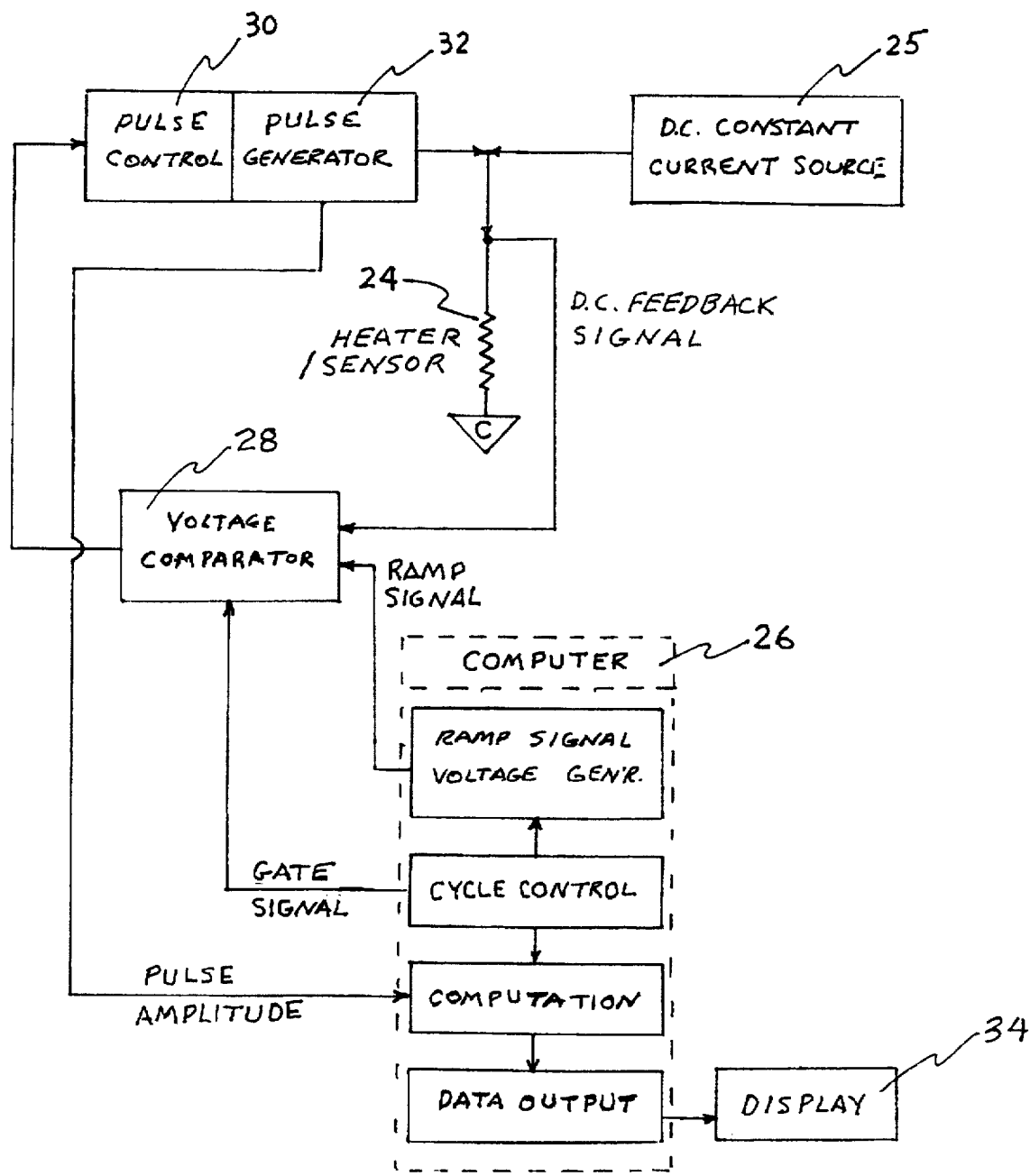
FIG. 5 illustrates alternative circuitry employed with a single heater/sensor element driven by a pulse generator.

In another embodiment of the invention, as shown in FIG. 5, the "heater" and "sensor" portions of the assembly are time-shared by the same element; i.e., this element is heated for some part of the measurement cycle and its temperature measured during some other part of the cycle, so two separate closely-coupled elements would not be needed. The element, indicated at 24 in FIG.5, may be a positive coefficient metal resistance wire connected to a constant current source 25. Any temperature increase of the element 24 results in an increased voltage drop across the element. This voltage is compared periodically with a ramp voltage generated by the computer 26 in voltage comparator circuit 28. The output of the comparator 28, by means of a pulse control circuit 30, determines the amplitude and/or pulse duration of energy pulses applied to the element 24 by a pulse generator 32. Pulse information is also fed to the computer 26 which in turn generates a gating signal to the comparator 28. The gating signal limits response to the temperature indicating input signal only to the time that no energy pulse is being applied to he heating/sensing element 24.

The computer 26 thus controls the time sharing of the element 24. Typically 90% of a measuring cycle is used to heat the fluid surrounding the element 24 in response to the output of the pulse generator 32. Any surge in the energy output of the pulse generator 32 is used by the computer to provide an output to a display 34. During the balance of the cycle the voltage comparator 28 is activated to make the temperature determination.

In this approach, the small, dedicated computer that must be a part of the system plays a major role in controlling the entire measurement process. The computer, through its "cycle control" capability, initiates and terminates the measuring cycle, causes energy either in the form of pulses to the heater/sensor element or as a continuous voltage for heating it, periodically switches from a heating mode to a measuring mode and back again, evaluates the energy level being fed to the heater/sensor element and determines if ice is or is not present by virtue of the energy requirements. Again, the criterion for making that judgment would be the presence or absence of an energy "surge" somewhere in the temperature range covered. In the event that a pulse mode of operation were preferred, the pulse generator might be one of three kinds, any one of which would serve the purpose:

1) a type where the input to the pulse generator from the comparator determines how many pulses of a given amplitude and duration will occur within a preset time period;

2) a type where the input to the pulse generator from the comparator determines what duration a pulse of a give amplitude will occupy within a preset time period;

3) a type where the input to the pulse generator from the comparator determines what amplitude a pulse of a given duration will reach within a preset time period.

By way of example only, the preset time period could be 100 milliseconds (ms) long and might be divided into (e.g.) 90 ms for application of power to heat the element, followed by 10 ms for measuring the element's temperature, followed by 90 ms of heating, etc. The temperature measurement signal would be fed back to the second input of the comparator, so that the difference between it and the input from the ramp generator would, suitably amplified, develop the output signal to drive the pulse control circuitry.

In addition to the two voltage input signals from the ramp generator and the heater/sensor element, as noted, the comparator receives a "gate control" signal from the computer. This gating signal causes the comparator to look at the input signals for comparison purposes only during the correct part of the preset time period—i.e., during the portion of that interval when the heating pulse was absent (10 ms in the example).

The comparator output increases as and if the temperature signal lags behind the ramp signal, thereby increasing the output of the pulse generator and so attempting to increase the temperature of the sensor and reduce this difference or error signal or error signal generated by the comparator 28. A measure of the energy being generated by the pulse circuit is fed back to the computer, where it enters into the computation required to determine if ice is or is not present. As in the previously disclosed embodiments, the temperature of the heater/sensor element would be driven upwards at a constant rate by a relatively constant amount of applied power, until the melting point of ice is reached. If ice is present, a large upsurge in energy required by the heater/sensor element occurs, in order to melt the ice in a very brief length of time; then the energy requirement drops to a much lower level again. However, and again as in other embodiments, no upsurge in required power would be observed if ice were not present. The computer takes into account the size of any upsurge in determining whether to report that ice was present or not, and at what rate it was forming if it were.

The heater/sensor element could be any sort of resistive metallic shape having a positive temperature coefficient (a thermistor, which has a negative temperature coefficient, could not easily be made to work), or it could even be a thermocouple. A resistive element would be best, as it could be made of an appropriate size and configuration to fit the surface of a wing, rudder, aileron, etc., and a computer could easily be programmed to generate a ramp signal closely matching the resistance-versus-temperature signal expected from the element, even if it were not linear.

A signal related to the heating pulse itself is returned to the computer as a means of determining how much energy is being fed to the heater/sensor element during any preset time period. The nature of this signal depends upon which of the three types of pulse circuits described above is in use, but it should be designed to convey to the computer the information necessary to calculate the power level being required by the element as a function of time, in order to determine the presence or absence of ice as previously described.

Figure 6:
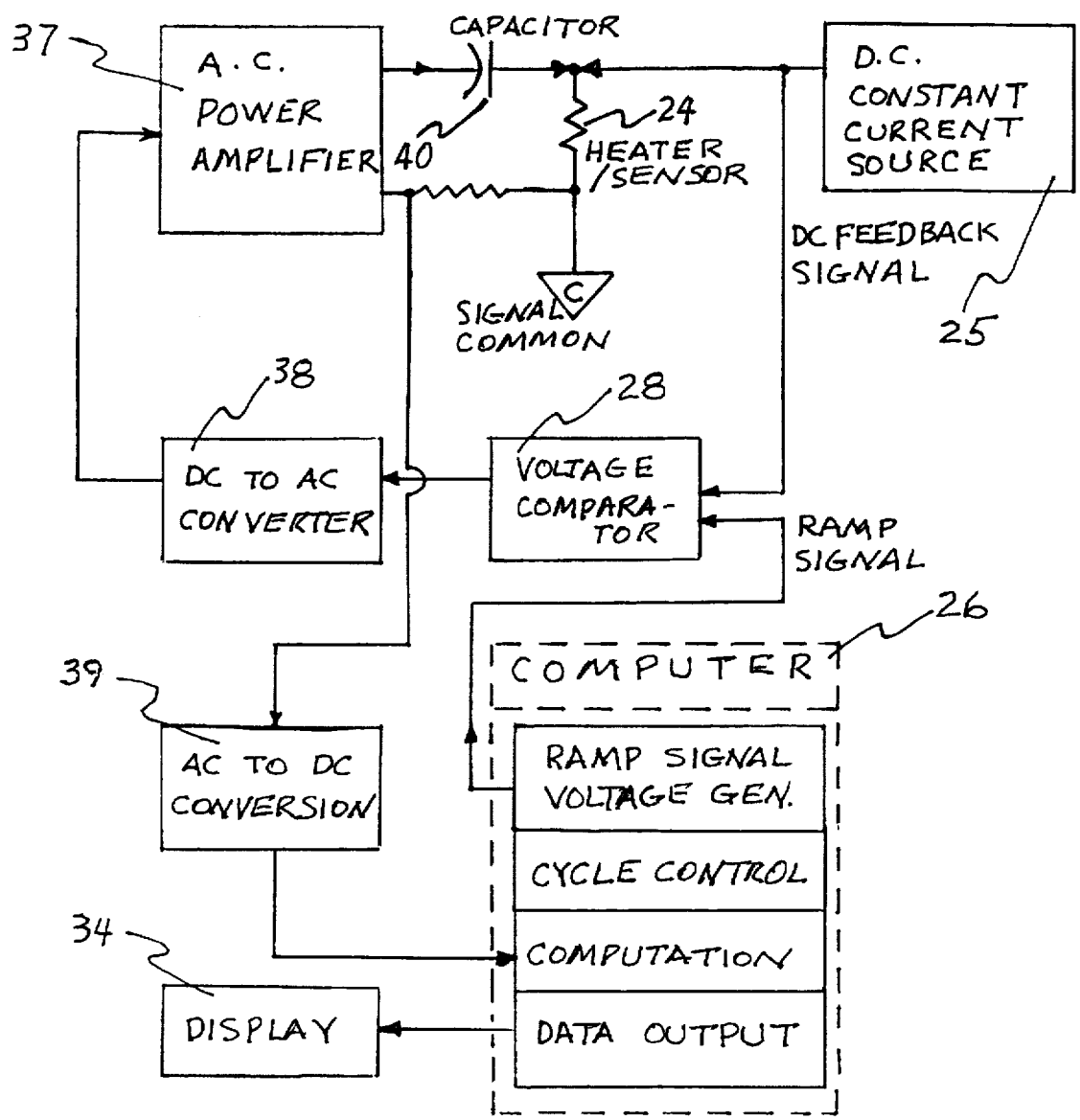
FIG. 6 illustrates typical circuitry employed with a single heater/sensor element driven by AC power and utilizing DC to AC and AC to DC converters.

A second means of utilizing a single heater/sensor element is also possible. In this embodiment, shown in FIG.6, the computer 26 again controls the various functions through its "Cycle Control" section and generates a ramp signal in order to cause a steady rise in temperature at the heater/sensor 24. No pulse generating circuit is required by this approach, however. Instead, the DC output of the voltage comparator 28, which represents the difference between the actual temperature of the heater/sensor element and the desired temperature as determined by the ramp voltage at the time, is fed to a DC-to-AC converter 38. The AC voltage resulting is amplified and then applied via a large capacitor 40 to the element to drive its temperature upwards. The capacitor serves to transfer the AC power for heating the element without interfering with the DC signal being generated by the element that in turn is being fed back to the comparator. In this approach, no timing "gate" is required; heating of the element 24 and measurement of its temperature could be carried out simultaneously. Again, either a resistive element or possibly a thermocouple might serve as the heater/sensor element, but a thermistor with a negative temperature coefficient would not seem to be practical.

In a finished state, the sensor/electronics combination should be able to operate with a very high ramp speed up to just below the melting point of ice (say, −2 degrees Centigrade), then ramp through the range −2 degrees to +1 degree in 5 seconds or less, and shut down to re-equilibrate after +1 degree. Total time to get a "reading" of the ice formation rate should take around 10 seconds; several per minute should be possible.

Although the present invention has been described in terms of preferred embodiments, those skilled in the art will realize that changes can be made in form and detail without departing from the basic method of detecting the presence of ice in a fluid sample, namely, forcing a constant rate of temperature increase through the freezing point by adjusting the level of energy input, and detecting any abrupt power changes signaling the presence of ice. When compared with known prior art, the present invention has the following advantages:

1. Answers regarding the question of how much, if any, ice is forming are obtained faster because there is virtually no time wasted waiting for ice to melt, which time could be very long with other methods if a large quantity of ice should be present. With the present invention, the melting of a large accretion of ice will produce a large signal, which is desirable, but will not increase the length of the measurement cycle, which would be undesirable.

2. Earlier patented inventions run the risk that, in a situation where the ambient temperature is very low and the measuring time very long, ice may accrete to the sensor surface even during the measuring step, leading to gross errors in estimating the rate at which icing is occurring. Or, in a very extreme case, if the rate of heat loss to the impinging air stream were to be very high, the heating power applied by a "constant power applied" system could fall below that required to raise the temperature at the sensing surface to the melting point of ice, thereby preventing the system from producing an answer at all.

3. The electronic circuitry required by the present invention is simpler and more reliable than that of the "constant power applied" inventions and most other, similar inventions.

4. The signal generated by this "constant rate of temperature increase" approach is completely unique in its ability to discern the presence or absence of ice, and is not prone to false alarms or failures to detect unsafe conditions.

What is claimed is:

1. Apparatus for detecting the presence of ice in a sample, comprising:

means for applying heat energy to the sample at an adjustable level to increase the temperature of the sample, temperature sensing means for detecting any changes in the temperature of the sample in response to the applied heat energy, the temperature sensing means generating a temperature indicative output, means responsive to said output of the temperature sensing means for adjusting the level of applied heat energy to maintain a predetermined rate of temperature increase of the sample, and means for detecting any abrupt change in the level of energy applied to the sample.

2. Apparatus of claim 1 further comprising:

means responsive to the energy level detecting means for signaling the presence of ice in the sample in response to an abrupt change in the applied energy level.

3. Apparatus of claim 2 wherein:

said means for applying heat energy includes a resistance heater and an electric power source connected to the resistance heater.

4. Apparatus of claim 3 wherein:

said temperature sensing means is positioned in close thermal contact with but electrical isolation from said resistance heater.

5. Apparatus of claim 3 wherein:

said temperature sensing means includes said resistance heater, the resistance of said resistance heater changing with changes in temperature, and means responsive to said changes in resistance for controlling said means adjusting the level of energy generated by the heater.

6. Apparatus of claim 3 wherein:

the temperature sensing means comprises a thermocouple.

7. Apparatus of claim 3 wherein:

the temperature sensing means comprises a resistance wire.

8. Apparatus of claim 1 wherein said means for adjusting the level of applied heat energy further includes:

- a ramp generator for generating an output signal of predetermined waveshape, and
- a comparator responsive to the output of the ramp generator and the temperature sensing means, the comparator generating an output corresponding to any difference between the output of the temperature sensing means and output of the ramp generator, and
- means responsive to the output of the comparator for adjusting the energy level applied to the sample by said means for applying heat energy.

9. A method of sensing the presence of ice in a fluid sample comprising the steps of:

applying heat energy to the sample at an adjustable level to induce melting of any ice present in the sample, sensing any increase in temperature of the sample as heat energy is applied to the sample, adjusting the level of heat energy applied to the sample so as to maintain the sensed increase in temperature at a predetermined rate, and sensing any abrupt change in the level of applied heat energy required to maintain said predetermined rate of temperature increase.

10. The method of claim 9 further comprising the steps of:

interrupting the application of heat energy to the sample when the temperature of the sample rises above the freezing point of the fluid sample, allowing the fluid sample to cool back to ambient temperature, and repeating the application of heat energy to the sample.

11. The method of claim 9 wherein:

the heat energy applying step and the temperature sensing step occur simultaneously.

12. The method of claim 9 wherein:

the heat energy applying step and the temperature sensing step occur alternately.

* * * * *